US005833955A

United States Patent [19]

Kleinberg et al.

[11] Patent Number: 5,833,955

[45] Date of Patent: Nov. 10, 1998

[54] DIAGNOSTIC TESTS TO ASSESS A PERSONS ORAL MALODOR CAPACITY AND POTENTIAL FOR DEVELOPING PERIODONTITIS

[75] Inventors: Israel Kleinberg, Smithtown; Milroy Codipilly, Coram, both of N.Y.

[73] Assignee: The Research Foundation of State University of New York, Stony Brook, N.Y.

[21] Appl. No.: 746,754

[22] Filed: Nov. 14, 1996

[51] Int. Cl.[6] .......... A61K 7/16

[52] U.S. Cl. .......... 424/49; 514/562

[58] Field of Search .......... 514/562; 424/49

[56] References Cited

U.S. PATENT DOCUMENTS

| | | | |
|---|---|---|---|
| 3,459,508 | 8/1969 | Miczka | 23/232 |
| 3,507,269 | 4/1970 | Berry | 128/2 |
| 4,080,170 | 3/1978 | Borkenstein | 23/232 |
| 4,119,089 | 10/1978 | Preti et al. | 128/2 |
| 4,689,214 | 8/1987 | Niles et al. | 424/49 |
| 4,713,164 | 12/1987 | Krietemeir et al. | 204/400 |
| 4,818,489 | 4/1989 | Gonner et al. | 422/84 |
| 5,348,734 | 9/1994 | Ratcliff | 424/53 |
| 5,468,777 | 11/1995 | France et al. | 514/562 |

FOREIGN PATENT DOCUMENTS

WO 94/14407 7/1994 WIPO .

OTHER PUBLICATIONS

Kleinberg et al., "Oral Malodor", Oral Biology and Medicine, vol. 1, Issue 4, pp. 247–259, 1990.

J. Carlsson, J.T. Larsen, M.–B. Edlund, "Peptostreptococcus Micros Has A Uniquely High Capacity To Form Hydrogen Sulfide From Glutathion" —*Oral Microbiol Immunol.* 1993: 8: 42–45.

I. Kleinberg and G. Westbay, "Oral Malodor" —*Oral Biology and Medicine*, vol. 1, Issue 4, pp. 247–259 (1990).

Sten Persson, Maj–Britt Edlund, Rolf Claesson, Jan Carlsson, "The Formation Of Hydrogen Sulfide And Methyl Mercaptan By Oral Bacteria" —*Oral Microbial Immunol.* 1990: 5: 195–201.

Ken Yaegaki and Kazuo Sanada, "Biochemical and Clinical Factors Influencing Oral Malodor in Periodontal Patients" —*J. Periodontal*, Sep. 1992, pp. 783–769.

*Primary Examiner*—Kevin E. Weddington
*Assistant Examiner*—Dwayne C. Jones
*Attorney, Agent, or Firm*—Darby & Darby

[57] ABSTRACT

Oral malodor and periodontitis are common problems affecting a large percentage of the population. The present invention provides a method of assessing an individual's oral malodor producing capacity and potential for developing periodontitis. In particular, the present invention is directed to identifying those individuals prone to oral malodor and periodontitis by measuring the formation of volatile sulfur compounds (VSC) and reduction in $E_h$ following a challenge with cysteine or cystine. A method of assessing the effectiveness of a dental therapeutic or device to treat oral malodor and/or periodontitis is also provided by this invention.

16 Claims, 5 Drawing Sheets

DIAGNOSTIC TESTS TO ASSESS A PERSONS ORAL MALODOR CAPACITY AND POTENTIAL FOR DEVELOPING PERIODONTITIS

FIELD OF THE INVENTION

Oral malodor and periodontitis are common problems affecting a large percentage of the human population. The present invention provides oral diagnostic tests to determine a person's oral malodor capacity and potential to develop periodontitis. In particular, the present invention provides an oral diagnostic test which measures the oral putrefaction potential of a patient following a cysteine or cystine challenge. A method of assessing the effectiveness of a dental therapeutic agent or device to reduce oral malodor and periodontitis is also provided by the present invention.

BACKGROUND OF THE INVENTION

Halitosis is the general term used to describe unpleasant breath emitted from a person's mouth regardless of whether the odorous substances in the breath originate from oral or non-oral sources. Oral malodor refers to the contribution of malodorous substances arising from oral sources. Oral malodor is primarily produced during oral bacterial putrefaction, a process whereby peptides and proteins are hydrolyzed by oral bacteria and the resulting amino acids are further catabolized. Oral bacterial putrefaction is the collection of biochemical processes that involves the degradation of peptides and proteins by the oral microbes into amino acids which are then further degraded into end-products that include some that are odorous and others that are harmful to the oral soft tissues.

It is generally recognized in the dental literature that the volatile sulfur compounds, hydrogen sulfide ($H_2S$), methylmercaptan ($CH_3S_5H$) and dimethylmercaptan ($(CH_3)_2S$) are major contributors of oral malodor. Persson et al. (1990) "The Formation of Hydrogen Sulfide and Methyl Mercaptan by Oral Bacteria", *Oral Microbiol. Immunol.,* 5:195–201. These malodorous volatile sulfur compounds (VSC) are generated during oral putrefaction of sulfur containing amino acids, either free or originating from peptides or proteins. Sulfur containing amino acids are readily available in saliva, dental plaque, gingival crevices, periodontal pockets, and desquamating mucosal epithelial cells. They may also be derived from proteinaceous food particles trapped between the teeth, lodged in the gingival crevices or found on the mucous membranes of the oral cavity, especially the tongue.

In addition to the volatile sulfur compounds, other odorigenic substances may be produced by the plaque bacteria. Indole and skatole are produced during the catabolism of tryptophan. Putrescine and cadaverine are produced during the catabolism of arginine and ornithine respectively, and odorous fatty acids such as butyric and valeric may be produced from several other amino acids. Researchers have found that the volatile sulfur compounds are often present in the head space and vapor of putrefied saliva and in individual samples of mouth air. Tonzetich J. (1977) "Production and Origin of Oral Malodor: Review of Mechanisms and Methods of Analysis." *J. Periodontology,* 48: 13.

Previous studies have suggested detecting halitosis by measuring the concentration of hydrogen sulfide and methyl mercaptan in a person's breath. For example, U.S. Pat. No. 3,507,269, describes a clinical device for diagnosing the various causative factors of halitosis, including measuring hydrogen sulfide and methyl mercaptan. These compounds were measured by inserting a device having an absorbent material containing a 2% solution of lead acetate. The concentration of hydrogen sulfide and methyl mercaptan were determined colorimetrically. These studies have not suggested, however, a way to measure an individual's capacity to produce oral malodor or potential to develop periodontitis. Moreover, previous studies have not described quantitative methods of measuring oral malodor and periodontitis potentials.

Oral malodor has been found to be involved in or associated with the pathogenesis of periodontal disease. Microbiological studies have demonstrated that periodontal pathogenic microorganisms readily degrade sulfur containing compounds. In particular, Gram-negative bacteria such as *Fusobacterium nucleatum* and *Porphyromonus gingivalis* were found to readily degrade sulfur containing amino acids and proteins to produce volatile sulfur containing compounds. These volatile sulfur compounds were found to increase the permeability of the oral mucosa and collagen solubility, and to decrease protein or collagen synthesis. Tonzetich J. (1984) "Effect of Hydrogen Sulfide and Methyl Mercaptan on the Permeability of Oral Mucosa", *J. Dent. Res.* 63:994. Additionally, patients with periodontal disease were shown to have an eight times greater concentration of volatile sulfur compounds compared to patients without periodontal disease. Yaegaki et al. (1992) "Bioclinical and Clinical Factors Influencing Oral Malodor in Periodontal Patients", *J. Periodontal.,* 63:783–787.

After an extensive survey of the amino acids and various peptides, it has been discovered in the present invention that cysteine and cystine are the major causative agents responsible for lowering the oxidation-reduction potential ($E_h$) of the oral cavity. An oral cavity with a low $E_h$ favors an ecological environment that enables Gram-negative bacteria in the mouth to grow, engage in oral putrefaction, and produce the undesirable conditions of oral malodor and periodontitis. It has been surprisingly discovered in accordance with the present invention that both the oral malodor producing capacity and the potential for developing periodontitis can be determined following an oral challenge with a mouth rinse containing cysteine or cystine.

Identifying the susceptibility of a person to a particular disease or physiologic condition has become an increasingly effective approach to combat various diseases in recent years. One of the earliest diagnostic tests of this type is the glucose challenge used to determine the ability of a person to utilize glucose and in turn, the potential of a person to develop diabetes. The present invention describes novel oral diagnostic tests for quantitatively measuring an individual's oral malodor producing capacity and potential for developing periodontitis. Until the advent of this invention, providing a patient with a quantitative analysis of their potential of developing oral malodor or periodontitis has not been readily available.

SUMMARY OF THE INVENTION

The present invention relates to an oral diagnostic test for determining the oral malodor producing capacity of a person by administering a mouth rinse containing cysteine or cystine and quantitatively measuring in vivo or in vitro the VSC produced in the oral cavity.

The present invention further relates to an oral diagnostic test for determining a person's potential to develop periodontitis by administering a mouth rinse containing cysteine or cystine and quantitatively measuring in vivo or in vitro the oxidation-reduction potential ($E_h$ ) of the oral cavity.

Another aspect of this invention is directed to a method of monitoring the effectiveness of a dental therapeutic or device to treat oral malodor or periodontitis comprising measuring in vivo the VSC or the $E_h$, respectively, of the oral cavity before and after the dental therapeutic administered or the dental device is employed.

DETAILED DESCRIPTION OF THE INVENTION

Figure 1:
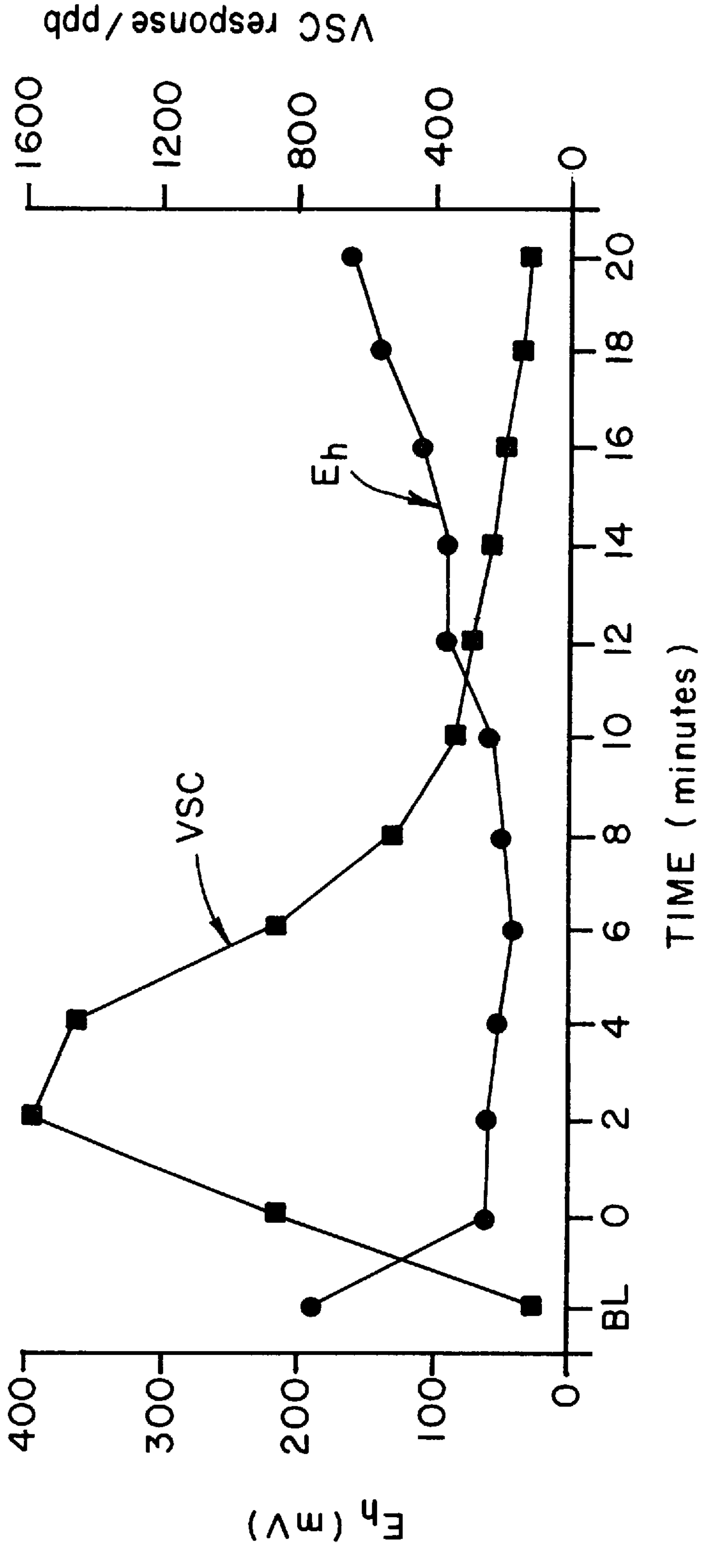
FIG. 1 shows the $E_h$, and VSC responses in vivo following a challenge with a 6 mM cysteine solution.

The essential components of the invention and relevant proportions of components are set forth below. All patents, publications and test methods mentioned herein are incorporated by reference.

The present invention is directed to methods of determining the oral malodor producing capacity of a person and his or her potential for developing periodontitis using various oral diagnostic tests. As defined by the present invention, the oral malodor producing capability is the ability of a person's oral flora to produce offensive oral malodor. Unlike previous oral malodor tests which qualitatively measure an individual's bad breath, the present invention provides a quantitative assay for measuring the potential of a person's oral flora to produce oral malodor. The potential for developing periodontitis may also be determined in accordance with the invention, by measuring the decrease in the $E_h$ following a mouthrinse containing cysteine or cystine.

The mouth rinses used in the oral diagnostic tests of this invention contain cysteine or cystine in a concentration generally ranging from approximately 3 mM to approximately 10 mM. In a preferred embodiment, the cysteine or cystine concentration in the rinse ranges from 5 mM to 6 mM. In addition to cysteine or cystine, the mouth rinse used in the methods of the present invention may also contain any conventional mouth rinse ingredient. (See U.S. Pat. Nos. 4,226,851; 4,209,754; 4,289,755; and 5,104,644). For example, the mouth rinse may contain a solvent such as distilled or deionized water, ethanol and the like; a sweetening agent such as saccharine, aspartame and the like; and a flavoring agent such as peppermint oil, spearmint oil and the like.

The pH of the mouth rinse generally ranges from about 6.0 to about 8.0. In a preferred embodiment, the pH ranges from about 6.5 to about 7.5. The pH of the mouth rinse described herein can be controlled with acid such as hydrochloric and with base such as sodium hydroxide or buffered with buffering agents such as sodium phosphate.

In the in vivo method of assessing a person's oral malodor capacity and potential for developing periodontitis, the $E_h$ and VSC of the oral cavity are initially determined. It is preferred that these measurements are done before the patient consumes any food or beverages or before oral hygiene, such as early in the morning.

The VSC of the oral cavity may be determined using a VSC indicator means, which is defined as any conventional technique capable of quantitatively measuring the VSC produced in the oral cavity. For example, the VSC may be quantitatively measured using a sulfide detector instrument such as a Halimeter Model RH-17A, Interscan Portable Analyzer). The Halimeter has a mouth piece attached to one end which pumps a person's breath into the instrument. A sulfur detector measures the VSC in the breath sample. In another embodiment, a small tube may be placed on the Halimeter to measure the VSC at specific sites in the oral cavity. The VSC of the oral cavity may be determined by calculating the average VSC level for the various sites analyzed.

The oxidation-reduction potential ($E_h$) of the oral cavity may be quantitatively measured using a platinum or gold electrode with a silver/silver chloride reference electrode connected to a pH meter wherein the pH meter is used as a millivoltimeter. The $E_h$ of various sites in the oral cavity such as periodontal pockets, the tongue and between the teeth, may be measured using an electrode connected to a millivoltimeter. The electrode is placed in these various sites and the $E_h$ is measured. The over-all $E_h$ of the oral cavity may be calculated by averaging the measurements of the various sites measured.

The mouth rinse may be administered for example, by having the patient rinse his/her mouth with approximately 5 to 10 ml of the cysteine or cystine mouthrinse for approximately 30 to 60 seconds and expectorate. The rinse may also be administered by straying the mouthrinse in the patient's mouth. Following the administration of the mouthrinse, there is generally a resting period of approximately two to five minutes before the VSC and/or $E_h$ are measured.

It has been discovered in accordance with this invention that a VSC level ranging from 0 to about 100 ppb is indicative of an oral flora with a normal oral malodor producing capability. A VSC level greater than 100 ppb has been found to be indicative of an oral flora with an oral malodor producing capability above normal. The greater the VSC level following the mouth rinse of this invention, the greater the capacity an individual has for producing oral malodor. With respect to periodontitis, an $E_h$, below approximately 40 to 50 MV has been found to be indicative of an oral flora capable of producing periodontitis. The lower the $E_h$ following the mouthrinse of this invention, the greater potential an individual has for developing periodontitis.

The present invention further provides an in vitro oral diagnostic test for quantitatively measuring a person's oral malodor producing capacity and potential for developing periodontitis. In one embodiment, a sample of whole saliva is collected from an individual using conventional techniques (e.g. chewing paraffin wax) and incubated at 37° C. with a cysteine or cystine solution for a time ranging from approximately 30 minutes to 8 hours. The incubation may be maintained at 37° C. using, for example, a water bath. The concentration of cysteine or cystine in the solution may range from approximately 3 mM to 10 mM and preferably between approximately 5 mM to 6 mM.

During the incubation, the VSC produced in the incubation mixture may be quantitatively measured using a VSC indicator means, such as a Halimeter. For example, samples of the air space in the incubation tubes may be collected using a small tube connected to the Halimeter and analyzed for VSC.

The $E_h$ of the incubation mixture may be quantitatively measured, for example, using a platinum or gold electrode with a silver/silver chloride or mercury/mercury chloride (calomel) reference electrode connected to a pH meter with or without a salt bridge wherein the pH meter is used as a millivoltimeter. The measuring end of the platinum or gold reference electrode system is placed in the incubation mixture. The Eh is quantitatively measured by comparing the $E_h$ of an incubation sample with and without a cysteine or cystine solution.

In another embodiment of the in vitro method, the saliva sample may be fractionated into salivary sediment and salivary supernatant prior to the incubation using conventional techniques such as centrifuging the saliva sample and decanting the salivary supernatant. (See, Ryan and Kleinberg (1995) *Arch. Oral Biol.,* 40, 743–752). Once the salivary sediment is separated from the supernatant, the sediment may be washed with distilled water before resuspending it at any desired concentration with the previously decanted or other salivary supernatant.

In a further embodiment of this invention, the oral malodor producing capacity may be measured in vitro by preparing an incubation mixture containing salivary sediment, salivary supernatant, phosphate buffer and cysteine or cystine. In one embodiment, the incubation mixture contains, for example, 16.7% (v/v) salivary sediment, 33.3% (v/v) salivary supernatant, 60 mM phosphate buffer and cysteine or cystine ranging from approximately 3 mM to approximately 10 mM. The incubation may be run for a time ranging from approximately 30 minutes to 8 hours. During the incubation, the VSC and the $E_h$ may be measured as described herein. Specifically, the VSC can be measured with a sulfide detector instrument such as an Halimeter and the $E_h$ may be measured using a platinum or gold $E_h$ electrode in conjunction with a silver/silver chloride calomel reference electrode connected to a pH meter used as a millivoltimeter.

A VSC level ranging from 0 to about 100 ppb has been found to be indicative of an oral flora with a normal oral malodor producing capability. In contrast, a VSC level greater than 100 ppb is indicative of an oral flora with an oral malodor producing capability above normal. The greater the VSC level, the greater the capacity an individual has for producing oral malodor. An $E_h$ below approximately 40 to 50 MV is indicative of an oral flora capable of producing periodontitis. The lower the $E_h$, the greater the potential an individual has for developing periodontitis.

The present invention has further identified a method of monitoring the effectiveness of a dental therapeutic or dental device to treat oral malodor and periodontitis by comparing the VSC and $E_h$ of the oral cavity following a mouth rinse containing cysteine or cystine prior to and subsequent to the administration of the dental therapeutic. In accordance with the method described herein, the VSC concentration of the oral cavity is initially measured to establish a baseline. The dental therapeutic is subsequently administered to the patient as directed to reduce or prevent oral malodor. To test the effectiveness of a dental device such as a toothbrush, dental floss, or a tongue scraper, to reduce the bacterial load and thereby reducing oral malodor the dental device is used as directed. The VSC concentration of the oral cavity is subsequently determined following the administration of the dental therapeutic or device. The measurement obtained is compared to the baseline measurement to calculate the VSC concentration. A decrease in the VSC concentration is indicative that the therapeutic or device is capable of reducing oral malodor. The greater the decrease in the VSC concentration, the more effective the therapeutic.

To determine the effectiveness of a dental therapeutic or device to treat periodontitis, a baseline $E_h$ is established by taking measurements throughout the oral cavity as previously described and averaging the measurements. A dental therapeutic is subsequently administered or the dental device is used as instructed. The $E_h$ of the oral cavity is measured and compared to the baseline measurement. An increase in the $E_h$ is indicative that the therapeutic or device is effective in reducing or preventing periodontitis.

In order to further illustrate the present invention, the experiments described in the following examples were carried out. It should be understood that the invention is not limited to the specific examples or the details described therein. The results obtained from the experiments described in the examples are shown in the accompanying figures and tables.

EXAMPLE I

This example describes an in vivo method of determining simultaneously the oral malodor producing capacity of a person and his/her potential to develop periodontitis. The patient examined in this study periodically suffered from oral malodor but did not have any clinical signs of periodontitis.

The VSC in the oral cavity, which arises mostly from the dorsal surface of the tongue, was measured using an Halimeter (Model RH-17A, Interscan Portable Analyzer) to determine the oral malodor producing capacity of a person. The potential of a person to develop periodontitis was determined by measuring the $E_h$ of the oral cavity. The $E_h$ of the dorsal surface of the tongue was measured using a platinum electrode with a silver/silver chloride reference electrode connected to the left forearm and both in turn were connected to a pH meter used as a millivoltimeter (Radiometer).

The VSC and $E_h$ of the oral cavity were initially measured to establish a baseline measurement. Following these measurements, a person was instructed to rinse with 5 ml of a 6 mM cysteine solution for approximately 30 to 60 seconds and expectorate. Approximately two to five minutes following the rinse, the VSC and the $E_h$ of the oral cavity were measured (FIG. 1).

The oral malodor producing capacity of a person was quantitatively determined by examining the amount of VSC produced following the rinse. The amount of VSC produced for a person with a normal oral malodor producing capacity is generally below about 100 to 200 ppb. An individual with an abnormal oral malodor producing capacity will readily degrade odorigenic substances to produce VSC at levels from approximately 100 to 200 ppb to as high as or higher than 1500 ppb. As shown in FIG. 1, the patient examined in this study has an high potential of producing oral malodor. The VSC levels were over 1500 ppb following a cysteine challenge rinse.

The potential for the patient studied in this example to develop periodontitis was determined by measuring the $E_h$ within the oral cavity following a cysteine challenge. The $E_h$ for a person without periodontitis or a potential developing periodontitis is generally above about 40 to 50 MV. A person with a potential for developing periodontitis generally has an $E_h$ below about 40 to 50 MV and as low as −200 MV. As shown in the data of FIG. 1, the patient studied did not have a great potential for developing periodontitis.

This study demonstrates that the potential of a person to produce oral malodor and develop periodontitis can be quantitatively measured. Moreover, shifts in oral flora affecting these parameters can be monitored over time to assess changes in a person's oral malodor producing capacity and potential for developing periodontitis.

EXAMPLE II

This example describes an in vitro method of determining simultaneously the oral malodor producing capacity and potential for a person to develop periodontitis. The patient examined in this study did not have any symptoms of oral malodor or periodontitis.

Whole saliva from a patient was collected, washed and separated as previously described by Kleinberg et al. (1973) *Archs. oral Biol.* 18, 787–798. An incubation mixture was prepared containing: 16.7% (V/V) salivary sediment, 33.3% (V/V) salivary supernatant, 60 mM phosphate buffer and 6 mM cysteine or cystine. The incubation was run for four hours in a water bath at 37° C. Following the incubation, the VSC of the incubation mixture was quantitatively measured using a Halimeter (Model RH-17A Interscan Portable Analyzer). The $E_h$ of the incubation was measured using a platinum electrode and a saturated potassium chloride salt bridge leading from a calomel reference electrode with both electrodes connected to a pH meter used as a millivoltimeter (Radiometer).

The oral malodor producing capacity of the patient was determined by examining the amount of VSC produced before and after degradation by the bacteria in the incubation of added cysteine. The amount of VSC produced for a normal person with low oral malodor producing potential is generally below about 100 to 200 ppb. An individual with an abnormal oral malodor producing potential will readily degrade odorigenic substances to produce volatile sulfur containing compounds at levels above approximately 100 to 200 ppb to as high as 1500 ppb.

Figure 2:
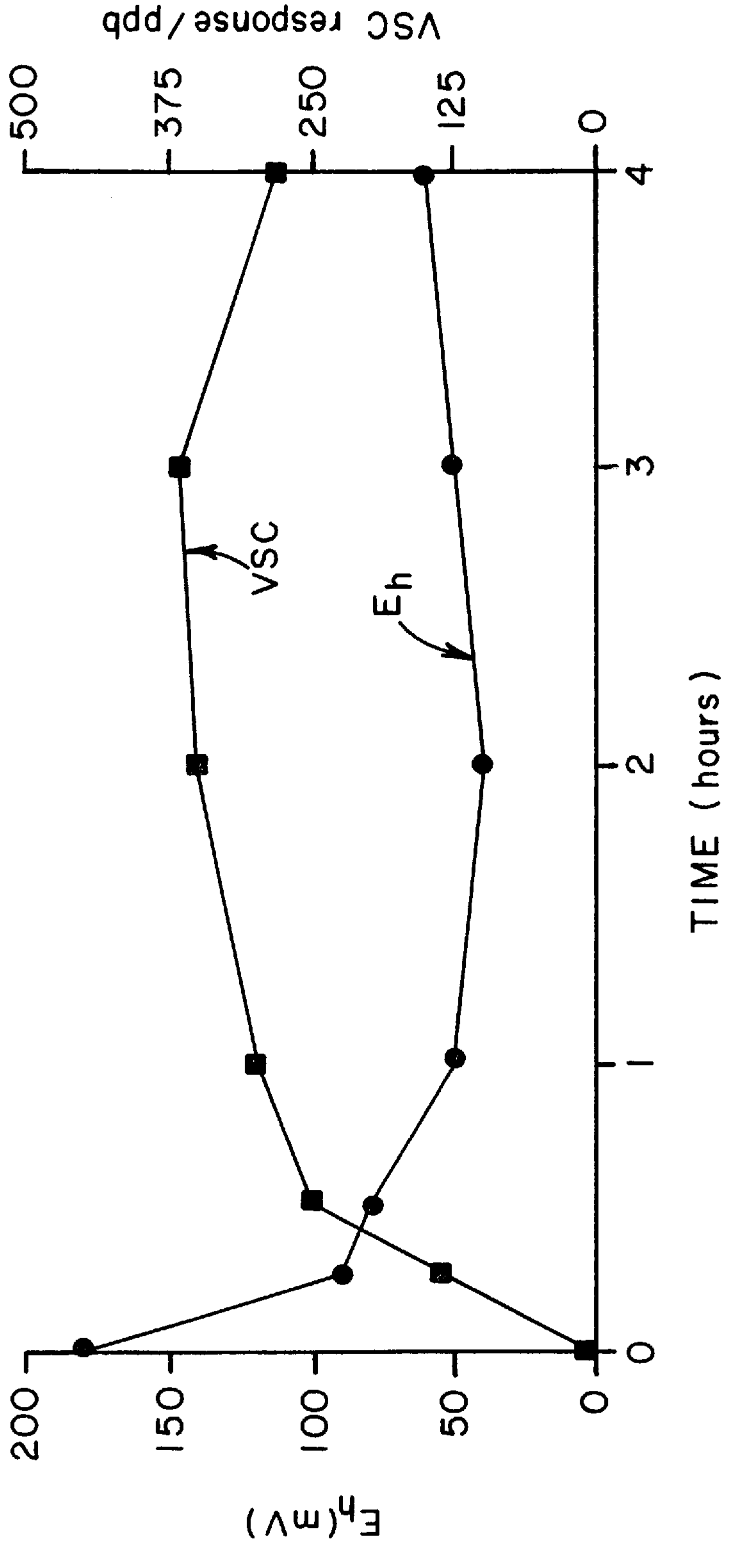
FIG. 2 shows the simultaneous $E_h$ and VSC responses in vitro following a challenge with a 6 mM cysteine solution.

The overall VSC produced during the incubation was calculated by subtracting the baseline VSC from the VSC produced following cysteine degradation. The results in FIG. 2 show a patient with a low oral malodor producing capacity.

A patients potential for producing periodontitis was determined by measuring the $E_h$ of the incubation mixture before and after a cysteine challenge to the incubation mixture. The $E_h$ for a person without periodontitis or a potential for developing periodontitis is generally above about 40 to 50 MV, while a person with a greater potential for having periodontitis generally has an $E_h$ below about 40 to 50 MV. The lower the $E_h$, the greater the potential for developing periodontitis.

The overall $E_h$ produced during the incubation is calculated by subtracting the baseline $E_h$ from the $E_h$ produced following the cysteine challenge. The potential for a person to develop periodontitis is determined by measuring the $E_h$ change during the incubation. As shown in FIG. 2, the patient examined did not show a significant potential of producing periodontitis.

EXAMPLE III

This example describes an in vivo method to determine the effectiveness of an oral therapeutic to treat oral malodor and to determine the effectiveness of improving its oral malodor reducing capability.

Figure 3:
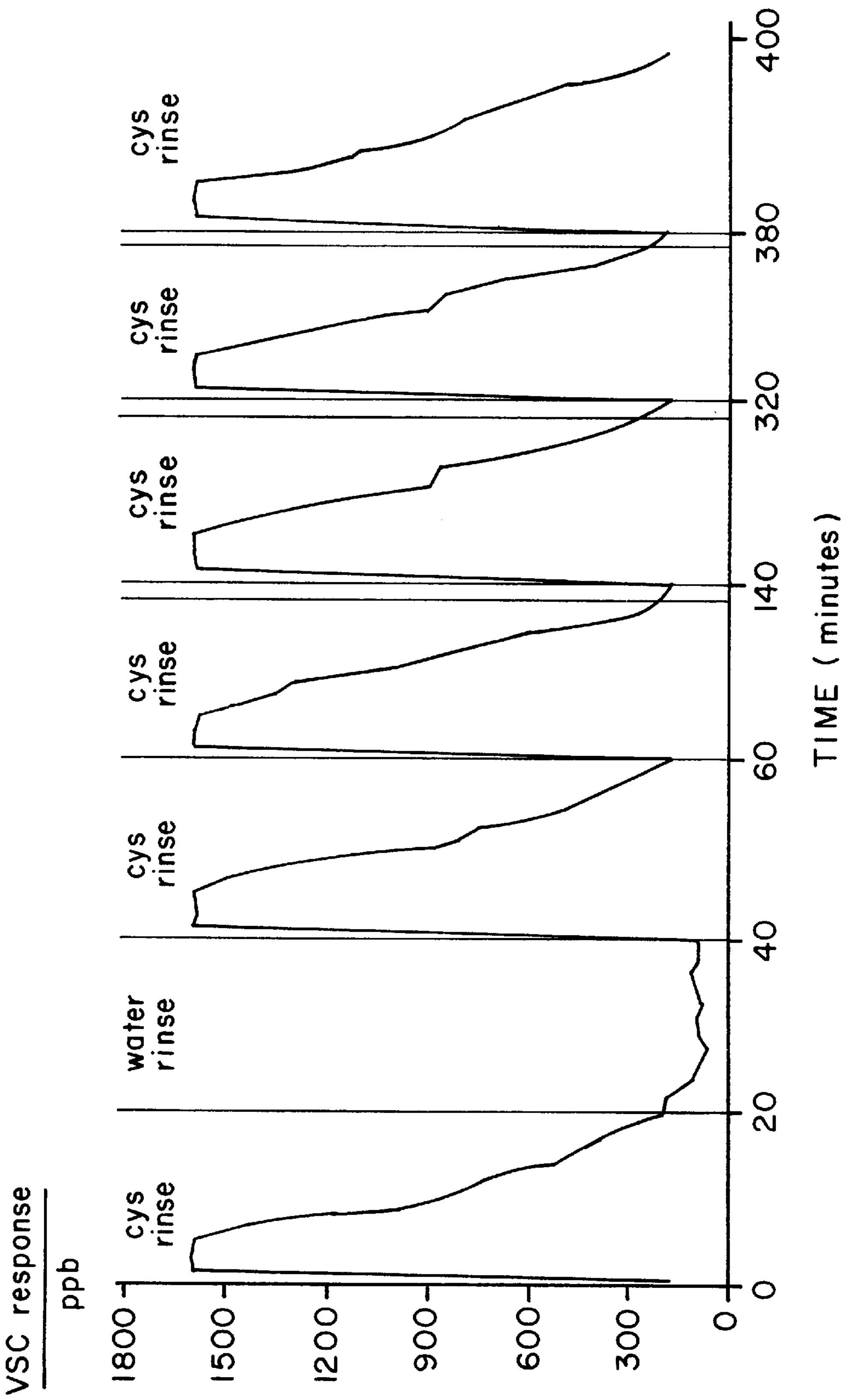
FIG. 3 shows the VSC produced in vivo of mouth air following repetitive challenges with a 6 mM cysteine solution.

According to this method, the baseline VSC level was measured as described in Example I and the person was instructed to rinse for 30 seconds with 5 ml of a 6 mM cysteine solution. The VSC was immediately measured after the rinse and subsequently at 2 minute intervals thereafter for 20 minutes. Following this cysteine challenge episode, the patient was instructed to rinse with water and VSC was measured again at 2 minute intervals for 20 minutes. Following the water rinse, the patient rinsed successively five times with 5 mM of the 6 mM cysteine solution and the VSC was measured as before. The water rinse served in this sample as a control. The successive cysteine rinses enable measurement of the oral malodor producing capacity of the oral bacteria and the duration of effectiveness of an oral therapeutic under test. The results for the water control which had no effect are shown in FIG. 3. As shown in FIG. 3, after each cysteine challenge, significant amounts of VSC were produced, indicating the patient is prone to oral malodor production.

Figure 4:
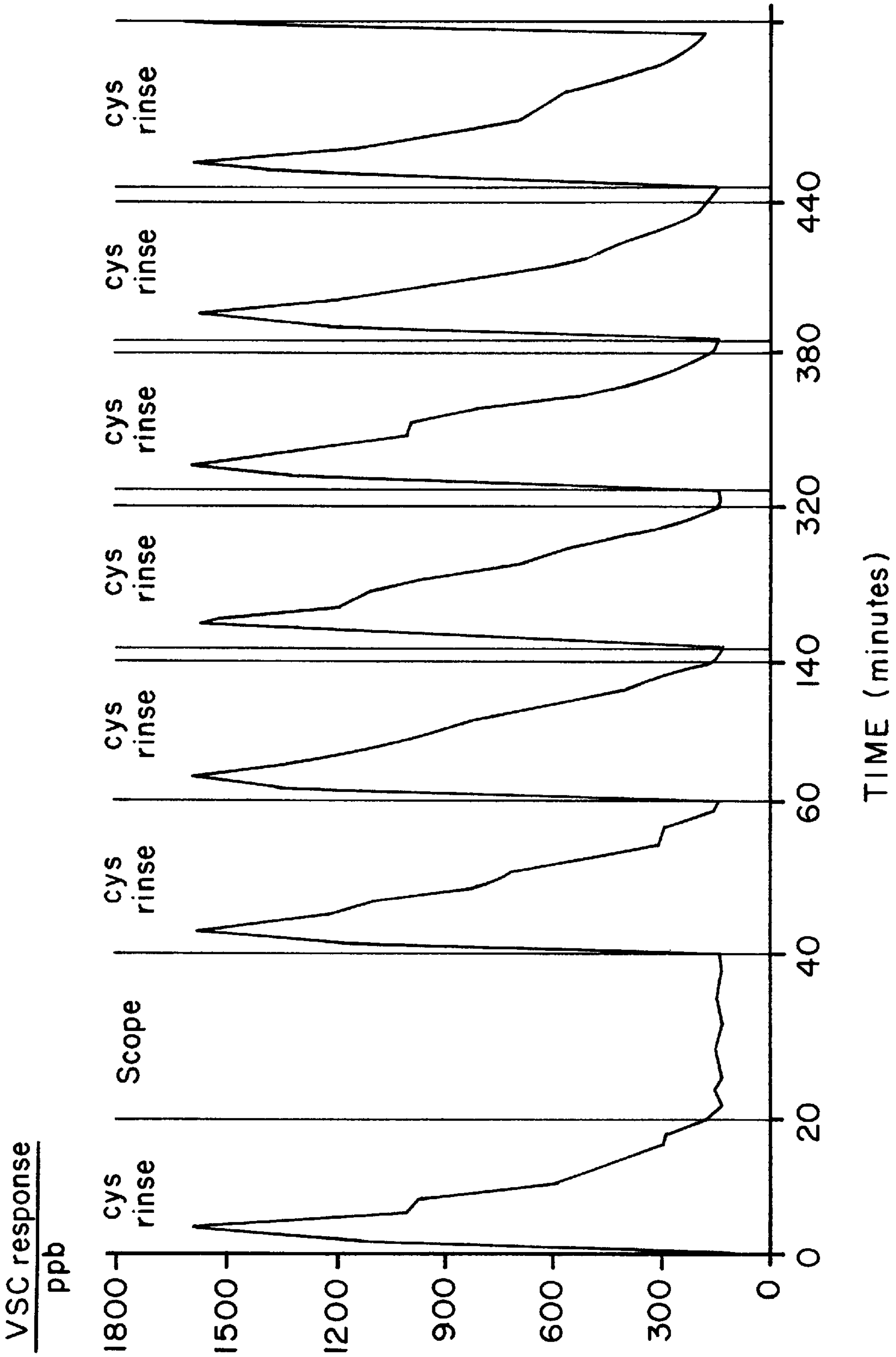
FIG. 4 shows the effect of a commercial mouthwash (Scope) on the oral malodor following a cysteine challenge in vivo.
Figure 5:
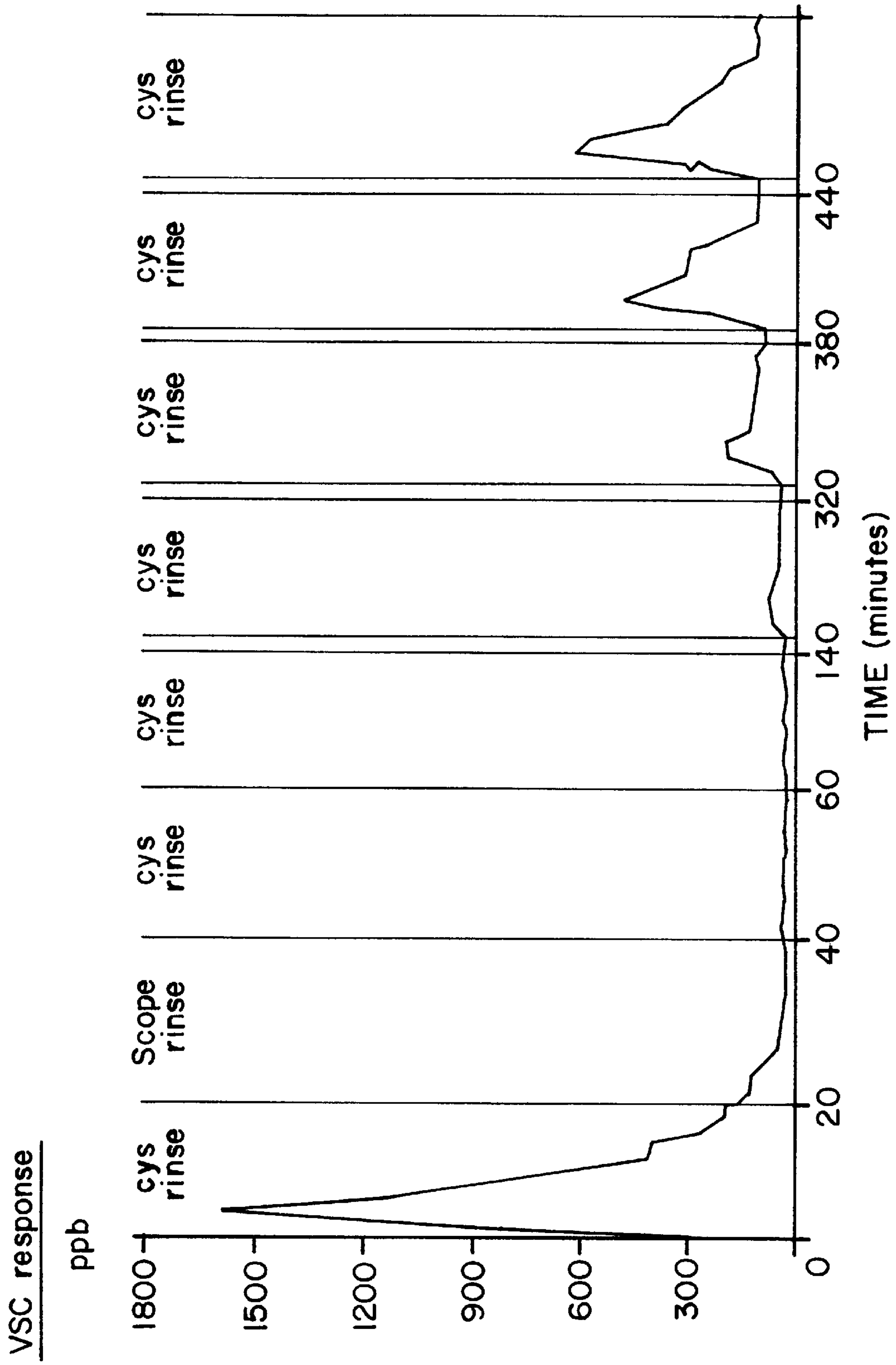
FIG. 5 shows the effect of a commercial mouthwash (Scope) plus zinc chloride on oral malodor following cysteine challenge in vivo.

Following the baseline measurements, a similar second series of rinses was run to test the effectiveness of the commercial mouth rinse SCOPE (FIG. 4). To test the effectiveness of zinc chloride to inhibit oral malodor production, it was added to the mouth rinse SCOPE at a concentration of 12 mM and tested. The results are shown in FIG. 5.

Water had no oral malodor reducing capability. The commercial mouthwash SCOPE also had little to no oral malodor reducing capability. Addition of zinc chloride dramatically reduced the malodor producing capability of cysteine. The reduction could be quantitatively measured over time. The duration of the reduction in VSC, as indicated by the delay in return to the baseline cysteine response, indicates that this rinse was effective in reducing VSC production over an extended period of time.

We claim:

1. A method of determining the oral malodor producing capacity of a person comprising rinsing the oral cavity with a mouth rinse containing cysteine or cystine and subsequently measuring the volatile sulfur compounds (VSC) produced in the oral cavity using a VSC indicator means.

2. The method of claim 1 wherein from approximately 5 to 10 ml of the mouth rinse is administered orally for 30 to 60 seconds.

3. The method of claim 1 wherein the mouth rinse contains cysteine or cystine in a concentration ranging from approximately 3 to 10 mM.

4. The method of claim 1 wherein the VSC indicator means is a sulfide detector instrument.

5. A method of determining the oral malodor producing capability of an individual comprising collecting a saliva sample, incubating the saliva sample at 37° C. with a solution containing cysteine or cystine for a time ranging from 15 minutes to 8 hours and measuring the volatile sulfur compounds produced using an indicator means.

6. The method of claim 5 wherein said cysteine solution contains cysteine or cystine in a concentration ranging from 3 to 10 mM.

7. The method of claim 5 wherein said indicator means is a sulfide detector instrument.

8. A method of determining the potential for a person to develop periodontitis comprising administering a mouth rinse containing cysteine or cystine to an individual and subsequently measuring the oxidation reduction potential ($E_h$) of the oral cavity using an $E_h$ indicator means.

9. The method of claim 8 wherein the mouth rinse is administered orally for 30 to 60 seconds.

10. The method of claim 8 wherein the oral rinse contains cysteine or cystine in a concentration ranging from approximately 3 to 10 mM.

11. The method of claim 8 wherein the $E_h$ indicator means is a platinum or gold electrode with a silver/silver chloride reference electrode or a mercury/mercury chloride reference electrode connected to a pH meter wherein the pH meter is used as a millivoltimeter.

12. A method of determining the potential of an individual to develop periodontitis comprising collecting a saliva sample from an individual, incubating the saliva sample at 37° C. with a solution containing cysteine or cystine for a time ranging from 15 minutes to 8 hours and measuring the $E_h$ of the incubated sample using an $E_h$ indicator means.

13. The method of claim 12 wherein the cysteine or cystine concentration in the solution ranges from approximately 3 to 10 mM.

14. The method claim 12 wherein said indicator means is a platinum electrode or gold electrode with a silver/silver chloride reference electrode or a mercury/mercury chloride reference electrode connected to a pH meter wherein the pH meter is used as a millivoltimeter.

15. An oral diagnostic kit for determining the oral malodor producing capacity of a person comprising a mouth rinse containing cysteine or cystine and a VSC indicator means.

16. An oral diagnostic kit for determining the potential of a person to develop periodontitis comprising a mouth rinse containing cysteine or cystine and an $E_h$ indicator means.

* * * * *